United States Patent [19]

Applegate

[11] 4,287,885
[45] Sep. 8, 1981

[54] KNEE BRACE WITH RESILIENT PAD SURROUNDING PATELLA

[75] Inventor: Leslie T. Applegate, Cincinnati, Ohio

[73] Assignee: Surgical Appliance Industries, Inc., Cincinnati, Ohio

[21] Appl. No.: 100,851

[22] Filed: Dec. 6, 1979

[51] Int. Cl.³ .............................................. A61F 5/01
[52] U.S. Cl. ....................................... 128/80 C; 2/24
[58] Field of Search ................. 128/80 C, 87 R, 80 R, 128/165, DIG. 15; 2/22, 24

[56] References Cited

U.S. PATENT DOCUMENTS

| 2,188,718 | 1/1940 | Jung | 2/24 |
| 2,524,326 | 10/1950 | Murphy | 128/24 R |
| 3,046,981 | 7/1962 | Biggs, Jr. et al. | 128/80 C |
| 4,099,269 | 7/1978 | Porner | 2/16 |
| 4,116,236 | 9/1978 | Albert | 2/24 |
| 4,201,203 | 5/1980 | Applegate | 128/80 C |

Primary Examiner—Robert W. Michell
Assistant Examiner—Arthur S. Rose
Attorney, Agent, or Firm—Wood, Herron & Evans

[57] ABSTRACT

A knee brace including an elastic sleeve stretchable circumferentially, a flexible sheet non-stretchable in a circumferential direction secured to the interior of the sleeve configured and dimensioned to surround a substantial portion of the user's patella, and a resilient pad stretchable at least circumferentially secured to the flexible inelastic sheet. By reason of the inelastic characteristics of the flexible sheet to which the resilient elastic pads are mounted, the pads are not circumferentially displaced or dislocated from their normal position proximate the periphery of the patella when the knee is bent and the elastic sleeve stretches circumferentially. Thus, patella support and protection is maintained regardless of the extent of knee flexure.

10 Claims, 4 Drawing Figures

U.S. Patent
Sep. 8, 1981
4,287,885
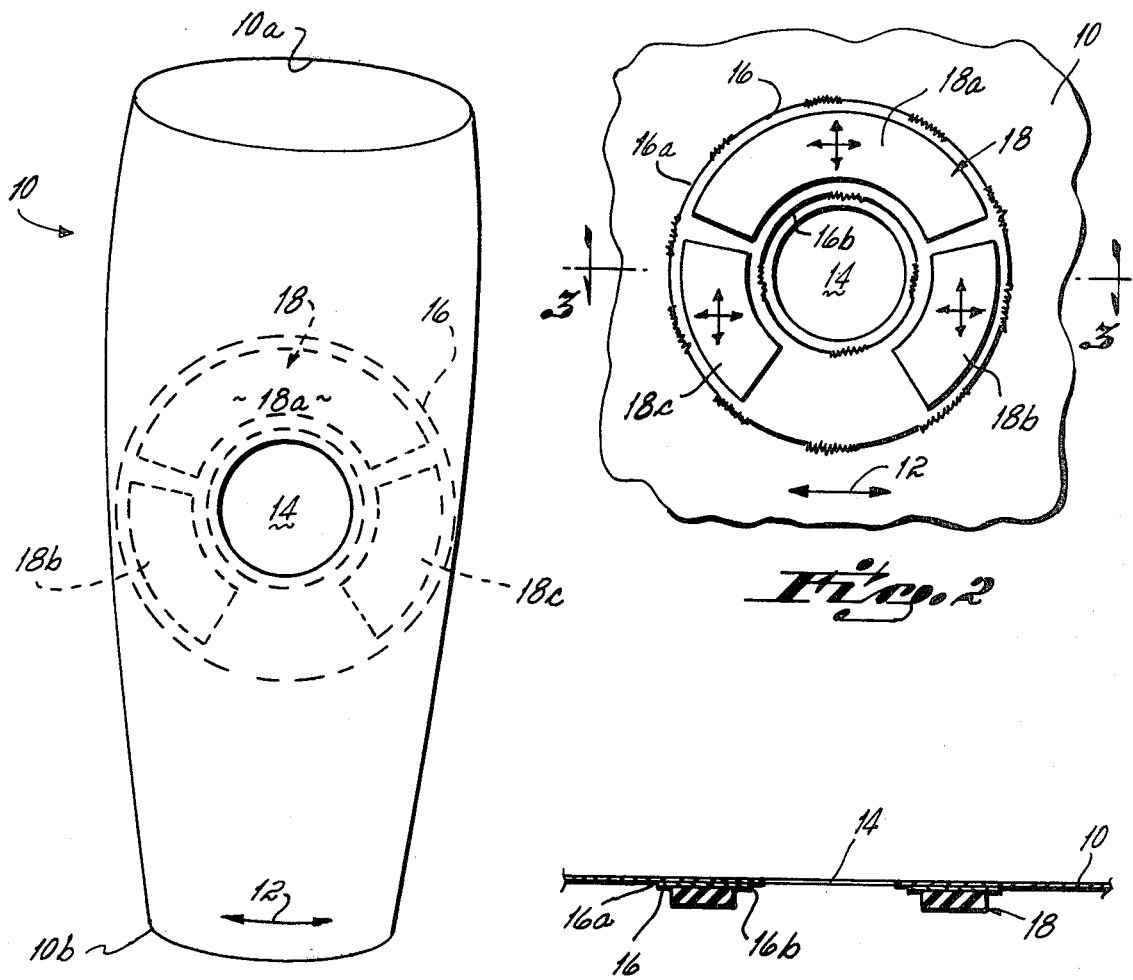
Fig. 1
Fig. 2
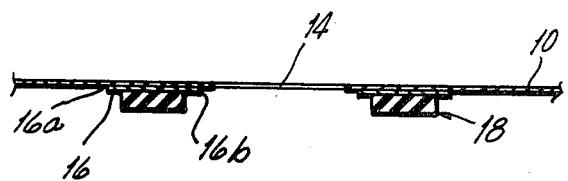
Fig. 3
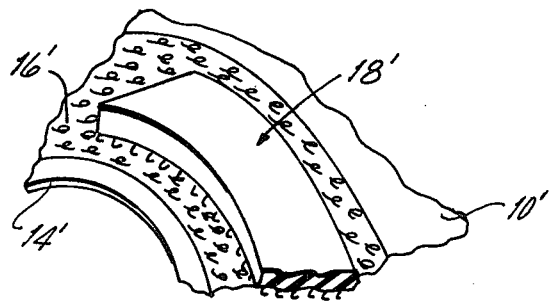
Fig. 4

KNEE BRACE WITH RESILIENT PAD SURROUNDING PATELLA

This invention relates to a knee brace of the type adapted to support an injured or weakened knee joint.

Knee braces consisting of elastic sleeves which apply compressive forces to the knee and have secured to the interior thereof resilient pads for protecting and supporting the patella, have existed in a variety of forms for many years. One of the principal objects in the design and construction of such knee braces is to ensure that whatever patella support and protection is designed into the knee brace is provided to the patella whether the leg is straight, partially bent, or fully bent. Thus, in a knee brace of the type having internal patella-supporting and protecting pads, wherein the pads are located and configured to snugly embrace the periphery of the patella, it is important that the pads remain in patella-enbracing relation throughout all possible conditions of the knee flexure. Since the prior art elastic sleeves to which the pads are customarily mounted tend to expand and distort in a circumferential direction when the knee is moved from a straightened position to a bent position, the pads displace or dislocate laterally relative to the patella. Hence, the prior art knee braces cannot maintain the designed degree of patella protection and support for all conditions of knee flexure.

Accordingly, it has been an objective of this invention to provide a knee brace of the type having an elastic sleeve and internal patella pads which is constructed to maintain the pads in patella-supporting and protecting relationship proximate the patella periphery regardless of the flexure condition of the knee joint. This objective has been accomplished in accordance with certain principles of this invention by providing, in combination with an elastic sleeve stretchable in a circumferential direction and internal pads surrounding a substantial portion of the patella, a flexible sheet non-stretchable in a circumferential direction which is secured to the interior of the elastic sleeve for providing a mounting means for the pads which is not stretchable in a circumferential direction when the sleeve stretches circumferentially as the knee is bent. By reason of the circumferential inelasticity of the flexible sheet to which the pads are mounted, when the knee is bent and the elastic sleeve expands and distorts circumferentially, the flexible sheet which mounts the pads does not expand or distort circumferentially, with the result that the pads are maintained proximate the periphery of the patella regardless of the degree of flexure of the knee, providing continued patella protection and support.

In accordance with a further aspect of the invention, the flexible sheet secured to the sleeve interior to which the pads are mounted is fabricated of circumferentially inelastic Velcro. The Velcro serves the dual purpose of preventing dislocation of the pads in a circumferential direction when the knee is flexed, and providing detachable and selectively variably positionable mounting of the pads relative to the patella.

These and other objects, advantages and features of the invention will become more readily apparent from a detailed description of the preferred embodiments thereof taken in conjunction with the drawings, in which:

FIG. 1 is a front elevational view in perspective of one embodiment of the knee brace of this invention;

FIG. 2 is a front elevational view of the interior of the front section of the knee brace shown in FIG. 1;

FIG. 3 is a cross-sectional view taken along line 3—3 of FIG. 2; and

FIG. 4 is an interior elevational view in perspective of a portion of the front section of another embodiment of the invention.

With reference to FIGS. 1—3, one embodiment of the knee brace of this invention is seen to include a generally tubular sleeve 10 of relatively elastic material which is preferably stretchable in only a horizontal, or circumferential, direction as indicated by the double-headed arrow 12. The circumference of the sleeve 10 is selected to snugly embrace the knee region of the wearer's leg when placed thereabout and provide compressive, radially inwardly-directed support forces to the wearer's knee. The longitudinal, or vertical, dimension of the sleeve 10 is selected to extend 3"–6" above and below the wearer's kneecap or patella. If desired, the knee brace may have a slight taper to it, with the circumference at the top 10a being greater than that at the bottom 10b, to more nearly conform to the tapered configuration of the wearer's leg in the region of the knee.

An opening 14 is, in a preferred form of the invention, provided in the front central section of the tubular sleeve 10. The opening 14 is dimensioned and configured to snugly embrace the perimeter, or marginal region, of the wearer's patella when the sleeve 10 is worn.

Permanently secured to the interior of the tubular sleeve 10 in the front thereof is a flexible sheet 16 which is inelastic in at least a horizontal, or circumferential, direction, and which is preferably also inelastic in a vertical, or longitudinal, direction. The inelastic sheet 16 is dimensioned and configured to surround a substantial portion, and preferably the entirety, of the patella opening 14. The inelastic sheet 16 may be fabricated of canvas, leather, a synthetic fabric, such as Dacron or Nylon, or the like, providing it possesses the desired inelasticity, at least in the circumferential direction. The inelastic sheet 16 is permanently secured to the interior of the front of the tubular sleeve 10 by any suitable means, preferably by stitching along the outer and inner edges 16a and 16b. Alternatively, the inelastic sheet 16 may be permanently secured to the sleeve 10 by a suitable adhesive.

Mounted to the interior surface of the flexible sheet 16 are pad means indicated generally by the reference numeral 18. The pad means surround a substantial portion, and preferably the entirety, of the patella opening 14, providing support and protection for the patella. The pad means 18 take the form of separate pad segments 18a, 18b and 18c which, except for the fact that they are attached to a common inelastic sheet 16, are physically separate and independent from each other. Alternatively, the pad means 18 may take the form of a single pad (not shown) having an annular or donut shape for completely encircling the patella opening 14, or a horseshoe shape (not shown) for encircling a substantial portion, but less than the entirety, of the patella opening 14. The pad means 18 are flexible and resilient, and in a preferred form have substantial elasticity in at least one direction, namely, circumferentially, and possibly also vertically. The pad means 18 may be secured to the flexible sheet 16 by any suitable means, such as stitching, adhesive, or the like.

An important advantage of using sheet 16, which is inelastic at least circumferentially, in combination with a sleeve 10, which is elastic at least in a circumferential direction, is that when the knee is bent the sheet 16 will maintain the pad means 18 in close proximity to the periphery of the wearer's patella. Were the inelastic sheet 16 omitted, and the pad means 18 mounted directly to the circumferentially stretchable elastic sleeve 10, the pad means would tend to shift or dislocate laterally, i.e., in a circumferential direction, when the knee is bent and the circumference of the tubular sleeve 10 increased. Such lateral displacement of the pad means 18 relative to the periphery of the wearer's patella reduces the support and protection provided by the pad means to the patella. However, with this invention, by securing the pad means to a circumferentially inelastic sheet 16 which in turn is secured to the circumferentially stretchable tubular sleeve 10, the pad means are not laterally or circumferentially displaced relative to the patella periphery when the knee is bent and the sleeve circumference increased. As a consequence, with this invention the desired support and protection of the patella is maintained even when the knee is bent.

In accordance with another embodiment of the invention, which is depicted in FIG. 4, the flexible inelastic sheet 16' is fabricated of Velcro, which is nonstretchable at least circumferentially. The Velcro sheet 16' is permanently secured to the inner surface of the tubular sleeve 10' in any suitable fashion. With the flexible, but inelastic, Velcro sheet 16' so secured to the inner surface of the tubular sleeve 10', the hook (or loop) fastening elements of the Velcro extend inwardly from the tubular sleeve for cooperation with Velcro loop (or hook) elements extending outwardly from the back of the resilient pad means 18' to which a sheet of Velcro is secured in any suitable means. Utilizing Velcro fastening means in the manner described, the cooperating sheets of Velcro not only function to facilitate securing the resilient pad means 18' in selectively variable positions relative to the patella opening 14', but also the Velcro sheet 16' serves the additional purpose of providing a flexible and inelastic anchor or mount surface for the pad means 18' so that when the knee is bent the pad means 18' will not be undesirably displaced, either circumferentially or longitudinally, relative to the patella.

I claim:

1. An improved knee brace comprising:
   a generally cylindrical sleeve formed of elastic material stretchable in a circumferential direction and dimensioned to cover the leg area at the knee joint, said sleeve having a central front patella section located to be proximate a wearer's patella when said sleeve is positioned about the wearer's knee,
   a flexible sheet of material substantially inelastic in a circumferential direction fixedly secured to the interior of said sleeve, said sheet configured and dimensioned to surround a substantial portion of said patella section of said sleeve, and
   a plurality of physically separate resilient pads secured to the interior surface of said sheet at spaced locations in a generally circular pattern to surround a substantial portion of said patella section of said sleeve, said pads being restrained by said sheet against circumferential movement relative to said patella section as said sleeve stretches under forces exerted thereon by the knee of a wearer thereof when bent.

2. The improved knee brace of claim 1 wherein said flexible sheet is substantially inelastic in a longitudinal direction to restrain said pads against longitudinal movement relative to said patella section of said sleeve when the wearer's knee is bent.

3. The improved knee brace of claim 2 wherein said sleeve is substantially inelastic in a longitudinal direction.

4. The improved knee brace of claim 1 wherein said sleeve is substantially inelastic in a longitudinal direction.

5. The improved knee brace of claim 1 wherein said sheet is fabricated of Velcro fastening material and said pads have cooperating Velcro fastening means for securing said pads to said Velcro sheet at selectively variable positions.

6. An improved knee brace comprising:
   a generally cylindrical sleeve formed of elastic material stretchable in a circumferential direction and dimensioned to cover the leg area at the knee joint, said sleeve having a central front patella section located to be proximate a wearer's patella when said sleeve is positioned about the wearer's knee,
   a flexible sheet of material substantially inelastic in a circumferential direction fixedly secured to the interior of said sleeve, said sheet configured and dimensioned to completely surround said patella section of said sleeve, and
   a resilient pad secured to the interior surface of said sheet, said pad configured and dimensioned to surround a substantial portion of said patella section of said sleeve, said pad being stretchable in a circumferential direction to at least approximately substantially the same extent as said sleeve, said pad being restrained by said sheet against circumferential movement relative to said patella section of said sleeve as said sleeve stretches under forces exerted thereon by the knee of a wearer thereof when it is bent.

7. The improved knee brace of claim 6 wherein said sleeve is stretchable in a longitudinal direction, said sheet is inelastic in a longitudinal direction, and said pad is stretchable in a longitudinal direction to at least approximately substantially the same extent as said sleeve, said pad being restrained by said sheet against longitudinal movement relative to said patella section of said sleeve as said sleeve stretches under forces exerted thereon by the knee of a wearer thereof when it is bent.

8. The improved knee brace of claim 6 wherein said sheet is fabricated of Velcro fastening material and said pad has cooperating Velcro fastening means for securing said pad to said Velcro sheet at selectively variable positions.

9. An improved knee brace comprising:
   a generally cylindrical sleeve formed of elastic material stretchable in a circumferential direction anddimensioned to cover the leg area at the knee joint, said sleeve having a central front patella section located to be proximate a wearer's patella when said sleeve is positioned about the wearer's knee,
   a flexible sheet of material substantially inelastic in a circumferential direction fixedly secured to the interior of said sleeve, said sheet configured and dimensioned to completely surround said patella section of said sleeve, and
   pad means secured to the interior surface of said sheet surrounding a substantial portion of said patella section of said sleeve, said pad means being restrained by said sheet against circumferential movement relative to said patella section of said sleeve as said sleeve stretches under forces exerted thereon by the knee of a wearer thereof when it is bent from a straightened position.

10. The improved knee brace of claim 9 wherein said sheet is fabricated of Velcro fastening material and said pad means have cooperating Velcro fastening means for securing said pad means to said Velcro sheet at selectively variable positions.

* * * * *